United States Patent
Grace et al.

[19]

[11] Patent Number: 6,082,858
[45] Date of Patent: Jul. 4, 2000

[54] APPARATUS AND METHOD OF MONITORING A SUBJECT'S EYES USING TWO DIFFERENT WAVELENGTHS OF LIGHT

[75] Inventors: Richard Grace; Robert K. Davis, both of Pittsburgh, Pa.

[73] Assignee: Carnegie Mellon University, Pittsburgh, Pa.

[21] Appl. No.: 09/301,996

[22] Filed: Apr. 29, 1999

Related U.S. Application Data

[60] Provisional application No. 60/083,509, Apr. 29, 1998.

[51] Int. Cl.$^7$ .................................................. A61B 3/00
[52] U.S. Cl. ............................................ 351/200; 257/440
[58] Field of Search ................................. 351/200, 206, 351/207, 213, 215, 221; 250/559.3; 257/440, 184; 356/73, 402, 407, 425

[56] References Cited

U.S. PATENT DOCUMENTS

| | | |
|---|---|---|
| 4,157,708 | 6/1979 | Imura . |
| 4,919,534 | 4/1990 | Reed ......................................... 356/73 |
| 4,922,919 | 5/1990 | Novack . |
| 4,953,111 | 8/1990 | Yamamoto et al. . |
| 5,138,416 | 8/1992 | Brillson ................................... 257/440 |
| 5,610,673 | 3/1997 | Rafal et al. . |
| 5,689,241 | 11/1997 | Clarke, Sr. et al. . |
| 5,801,390 | 9/1998 | Shiraishi .............................. 250/559.3 |

OTHER PUBLICATIONS

Yoshinobu Ebisawa, "Unconstrained Pupil Detection Technique Using Two Light Sources and the Image Difference Method."

Primary Examiner—George Manuel
Attorney, Agent, or Firm—Kirkpatrick & Lockhart LLP

[57] ABSTRACT

A device and method for monitoring a subject's eyes. The device includes a light source producing light of a first wavelength and producing light of a second wavelength, and the device includes at least one image sensor positioned to receive light reflected from the subject's eyes. The at least one image sensor produces a first signal indicative of light of the first wavelength and produces a second signal indicative of light of the second wavelength. The device may include a controller connected to the at least one image sensor and receiving the first and second signals. The controller may subtract the first signal from the second signal and produce a third signal indicative thereof. The controller may also provide a synchronization signal to the at least one image sensor and may also provide the signal to other components, such as the light source. One or more filters may be provided in the path of the reflected light so as to filter the light before it reaches the at least one image sensor. One or more lens may also be provided to focus the reflected light before the reflected light reaches the at least one image sensor.

61 Claims, 4 Drawing Sheets

APPARATUS AND METHOD OF MONITORING A SUBJECT'S EYES USING TWO DIFFERENT WAVELENGTHS OF LIGHT

CROSS REFERENCE TO RELATED APPLICATIONS

This application claims priority from provisional U.S. patent application Ser. No. 60/083,509 filed Apr. 29, 1998.

STATEMENT REGARDING FEDERALLY SPONSORED RESEARCH OR DEVELOPMENT

Certain of the research leading to the present invention was sponsored by the U.S. Department of Transportation under Department of Transportation contract number DTNH22-93-D07007, and Contract name "Crash Avoidance Research Technical Support Sensor Technology". The United States Government has certain rights in this invention.

BACKGROUND OF THE INVENTION

1. Field of the Invention

The present invention is directed generally to an apparatus and method of monitoring a subject's eyes and, more particularly, to an apparatus and method using light of two different wavelengths to monitor a subject's eyes.

2. Description of the Background

It is known in the art to monitor a subject's eyes, such as to measure "perclos". Perclos, generally, is a measure of the proportion of time that a subject's eyes are closed, either completely or beyond a predetermined point. For example, perclos may be the measure of the proportion of time that a subject's eyes are between 80% and 100% closed. Often, the measurement of perclos must be done manually, such as by videotaping the subject, reviewing the tape, and measuring the subject's perclos. Such a method, of course, is not practical for many applications.

Another method of determining perclos involves the use of an image sensor, such as a video camera, and image processing software to monitor the subject, determine the location of the subject's eyes, and determine the subject's perclos. That method, however, is time consuming and often cannot be performed in real time, thereby prohibiting it from being used to determine the drowsiness of a driver of a motor vehicle. One attempt to overcome that problem is to monitor only a portion of the subject's face, the portion containing the subject's eyes, thereby reducing the amount of processing required to determine perclos. That approach, however, creates another problem. The problem arises because the subject's eyes must be tracked as they move to monitor the road and as the subject's head and body move. Often, however, the subject moves quickly and the subject's eyes cannot be tracked. As a result, the prior art devices must search for the subject's eyes and, until the subject's eyes are located, the prior art devices cannot determine perclos.

Another deficiency with the prior art, regardless of whether the subject's entire face or only the subject's eyes are monitored, is that the prior art devices have difficulty finding and monitoring the subject's eyes. For example, the prior art devices often cannot distinguish between the subject's eyes and other sources of light and reflected light, such as is caused by dashboard lights, lights from other vehicles, and street lights. Those problems are exaggerated when the subject is wearing glasses.

Therefore, there is a need for a device and method for monitoring the eyes of a subject, such as can be used to determine perclos. The need exists for such a device and method that can operate in real time, can monitor the entire face of the subject, and is insensitive to other sources of light.

BRIEF SUMMARY OF THE INVENTION

The present invention is directed to a device and method for monitoring a subject's eyes. The device includes a source of light producing light of a first wavelength and producing light of a second wavelength, and the device includes at least one image sensor positioned to receive light reflected from the subject's eyes. The at least one image sensor produces a first signal indicative of light of the first wavelength and produces a second signal indicative of light of the second wavelength. If the device includes only one image sensor, the first and second wavelengths of light may be strobed. Alternatively, the first and second wavelengths of light may be constant, and filters may be used to separate the light. If the device includes two image sensors, one image sensor may produce the first signal and the other image sensor may produce the second signal. The device may include a controller connected to the at least one image sensor and receiving the first and second signals. The controller may subtract the first signal from the second signal and produce a third signal indicative thereof. The controller may also provide a synchronization signal to the at least one image sensor and may also provide the signal to other components, such as the light source. One or more filters may be provided in the path of the reflected light so as to filter the light before it reaches the at least one image sensor. One or more lens may also be provided to focus the reflected light before the reflected light reaches the at least one image sensor. The present invention may also include a feedback device, such as an audible alarm, that is controlled by the controller.

The present invention also includes a method. The method includes illuminating the subject's eyes with a first wavelength of light and illuminating the subject's eyes with a second wavelength of light. The method also includes sensing light of the first wavelength and providing a first signal indicative thereof, sensing light of the second wavelength and providing a second signal indicative thereof, and providing a third signal indicative of the first signal subtracted from the second signal. The method may also include providing a synchronization signal to the image sensors. If the subject is, for example, determined to be drowsy, a stimuli signal may be provided. That signal may be provided to a feedback device, such as a audible alarm.

The present invention solves many of the problems in the prior art. For example, the present invention allows for the entire face of a subject to be monitored while greatly reducing the amount of data processing. As a result, the present invention allows eye monitoring in real time with little risk of "losing" the subject's eyes. Furthermore, the present invention eliminates false signals caused by environmental interference, such as from dashboard lights, lights from passing cars, and street lights. The present invention is also unaffected by eye glasses. Those and other advantages and benefits of the present invention will become apparent from the DETAILED DESCRIPTION OF THE INVENTION hereinbelow.

BRIEF DESCRIPTION OF THE SEVERAL VIEWS OF THE DRAWING

For the present invention to be clearly understood and readily practiced, the present invention will be described in conjunction with the following figures, wherein.

DETAILED DESCRIPTION OF THE INVENTION

Figure 1:
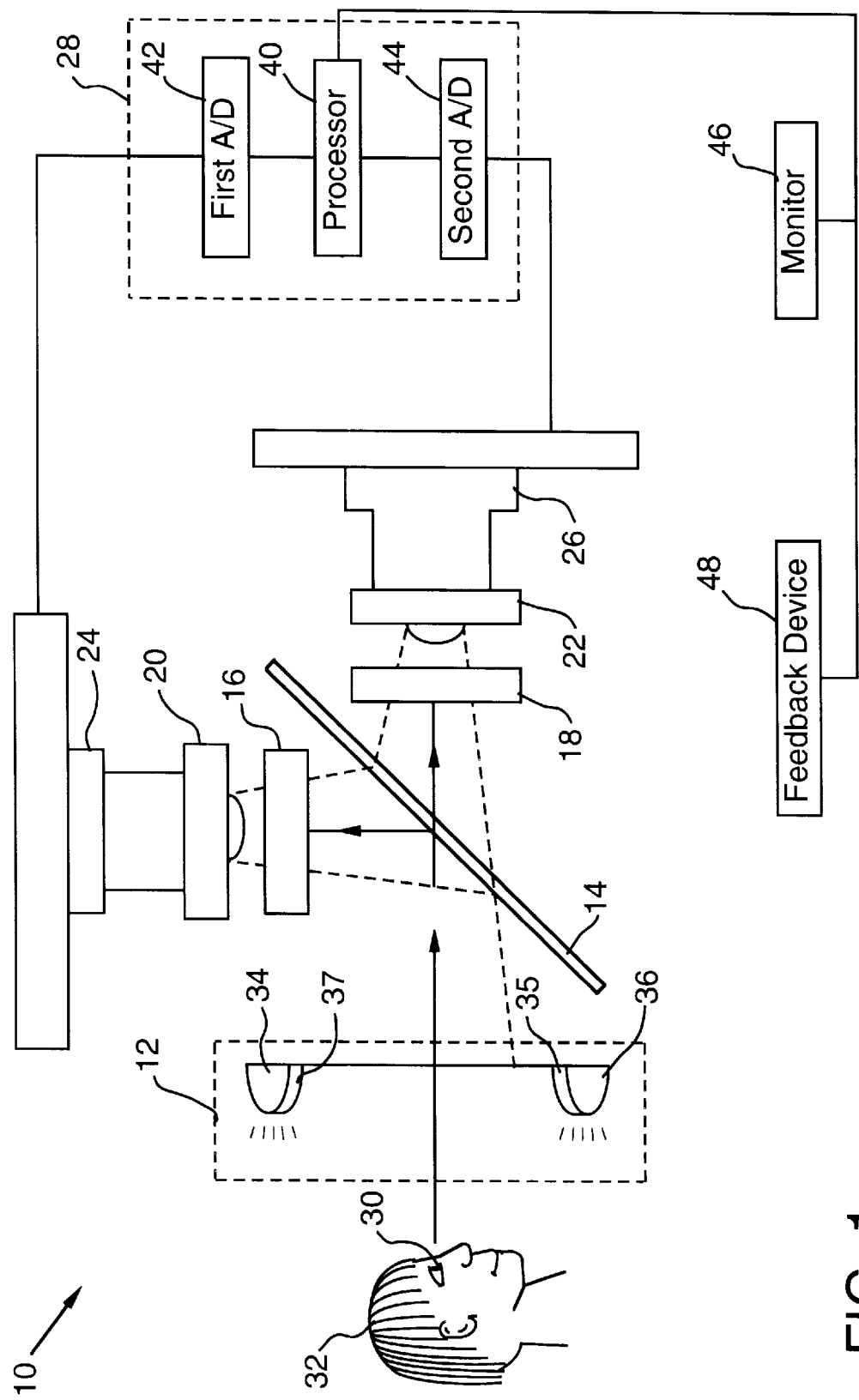
FIG. 1 is a combination block diagram and circuit schematic of a device constructed according to the present invention.

The present invention measures a subject's eye using two or more different wavelengths of light. The present invention will be described in terms of two different wavelengths of light, although more than two wavelengths may also be used. Generally, light is reflected by the different components of the eye. However, in the light spectrum there are peaks and valleys in the reflection/absorption characteristics. Some wavelengths of light, such as about 850 nm, are largely reflected, while other wavelengths demonstrate significant absorption. One wavelength in particular, about 950 nm, is largely absorbed. It has been found that by using light having two different wavelengths, with each wavelength having different reflection/absorption characteristics, useful measurements, such as perclos, can be obtained. It has also been found that two wavelengths, about 950 nm and about 850 nm, are particularly useful in that regard, although other wavelengths may provide superior results. Aside from the significantly different retinal reflection/absorption characteristics of 950 nm light and 850 nm light, however, they produce images of a human face that that are nearly identical. As a result, two images formed from light of 950 nm and 850 nm, respectively, are approximately identical to each other except that the image formed from light having a wavelength of about 950 nm will not have an image (or will have a very faint image) of the subject's pupils.

The wavelengths of 950 nm and 850 nm are only an example of two wavelengths that may be used in the present invention, and are not limitations of the invention. Other wavelengths, having different reflection/absorption characteristics, may also be used. As a general guideline, the light used should not be pupil restricting, should not be damaging to the subject, and should not be distracting (e.g. it should not be visible to the subject). Infrared light generally is a good choice, although other wavelengths may also be used. The extent to which the reflection/absorption characteristics of two wavelengths must differ for use with the present invention depends on the sensitivity of the equipment being used. Furthermore, although the retina generally provides the greatest variance of reflection/absorption, the other parts of the eye, such as the lens, vitreous, and the aqueous portions, also exhibit reflection/absorption characteristics that may be used with the present invention. Although the present invention will often be described with respect to the retina and infrared light, the present invention may be used with the other portions of the eye and with other wavelengths.

The present invention may be used in many ways, including to determine perclos and as a gaze tracker. The present invention has many applications, including use in automobiles to reduce the risk that the driver will fall asleep at the wheel. Another application is in commercial motor vehicles, such as large truck and vehicles carrying hazardous materials. The present application may also be used for paraplegic communications, and human factors studies. The present invention will be discussed with respect to determining perclos, although one of skill in the art will understand from that description that the present invention has many other applications.

FIG. 1 is a schematic drawing illustrating a device 10 constructed according to the present invention. The device 10 includes a light source 12, a beamsplitter 14, first and second filters 16, 18, first and second lens 20, 22, first and second image sensors 24, 26, and a controller 28. The device 10 may be used to monitor the eyes 30 of a subject 32.

The light source 12 produces at least two wavelengths of light. The first wavelength may be about 950 nm, and the second wavelength may be about 850 nm. The source of light may be formed from a plurality of light emitting diodes ("LED"s) 34, 35. For example, one LED 34 may produce a wavelength of light of about 950 nm, and the other LED 35 may produce a wavelength of light of about 850 nm. The source of light 12 may include a plurality of LEDs 34–37 producing each wavelength of light, such as two LEDs 34, 36 producing a wavelength of light of about 950 nm, and two LEDs 34, 37 producing a wavelength of about 850 nm. Of course, more than two LEDs for each wavelength may also be used. The LEDs may be formed in a ring so that light produced by the LEDs 34–37 is incident upon and reflected by the eye 30, and the reflected light passes through the ring formed by the LEDs 34–37, as illustrated in FIG. 1. The light source 12 may produce both the first and second wavelengths at about the same intensity, or it may produce one wavelength at a higher intensity than the other, such as to compensate for insensitivity of one of the wavelengths. An eye 30 tends to reflect light at approximately the same angle at which the light is incident onto the eye 30. As a result, the reflected light tends to follow a path that is very similar to the path of the incident light. Accordingly, the light source 12 may be positioned close to and around a desired path into the device 10 for the reflected light, so that there is only a small angle between the incident light and the reflected light.

The beamsplitter 14 may be a 50/50 beamsplitter tuned to direct about half of the reflected light into the first filter 16, and about half of the reflected light into the second filter 18. Beamsplitters 14 that are other than 50/50 beamsplitters may also be used, such as if it is desired to provide more of the reflected light to one of the first and second filters 16, 18. The beamsplitter 14 may be, for example, a metallized beamsplitter. The beamsplitter 14 may also be a dichroic beamsplitter. A dichroic beamsplitter is generally much more efficient than a metallized beamsplitter, thereby making more light available for processing and requiring less light for proper operation.

The first and second filters 16, 18 pass light of the first and second wavelengths, respectively. For example, the first filter 16 may pass light with a wavelength of about 950 nm, and the second filter 18 may pass light having a wavelength of about 850 nm. As a result, the first and second filters 16, 18 provide that only selected light is passed to the lens 20, 22 and the image sensors 24, 26. The first and second filters 16, 18 may be, for example, dielectric filters, and may have a 50 nm half power band width.

The first and second lens 20, 22 focus the light passing through the first and second filters 16, 18, respectively, so that a clear image may be received by the first and second image sensors 24, 26. The first and second lens 20, 22 may be separate elements of the device 10 or they may be integral to the first and second image sensors 24, 26.

The first and second image sensors 24, 26, receive the light focused by the first and second lens 20, 22, respectively. The first and second image sensors 24, 26 provide first and second signals, respectively, that are indicative of the images received by the image sensors 24, 26. The first and second image sensors 24, 26 may be, for example, charge coupled devices ("CCD") or a CMOS-type devices.

To facilitate the production of more identical images from the first and second image sensors 24, 26, the image sensors 24, 26 may be synchronized using a common synchronization signal, such as may be provided by the controller 28, so that each frame or image from the first image sensor 24 is taken at the same point in time as an image from the second image sensor 26. In other words, the synchronization signal facilitates the production of a pair of corresponding images, one from the first image sensor 24, the other from the second image sensor 26, both taken at the same point in time. As a result, differences due to changes in the subject 32 with time, such as changes in expression and movement of the subject 32, may be eliminated.

The present invention takes advantage of the fact that light reflected from the subject's retina returns along the same path as the incident light from the light source. As a result, retinal reflection will be available to a fixed device 10 (such as a device 10 fixed on an automotive dashboard), even when the subject is looking over a wide range of angles. It has been found that reflected light is available over a range of incident beams as much as about 70 degrees off axis.

The controller 28 receives first and second signals from the first and second image sensors 24, 26, processes those signals, and produces a signal indicative of that processing. The controller 28 may include a processor 40, such as a Pentium PC104 ("Pentium" is a registered trademark of Intel Corporation, Santa Clara, Calif.). If the first and second image sensors 24, 26 provide an analog output signal, as opposed to a digital output signal, first and second analog-to-digital converters 42, 44 may be provided to convert the output signals from the first and second image sensors 24, 26, respectively, to digital signals for use by the processor 40. If the processor 40 does not require a digital signal, the converters 42, 44 may be omitted. The controller 28 may provide one or more of the first, second, and third signals to a video monitor 46 to display one or more images represented by those signals. The controller 28 may also provide a signal to a feedback device 48, such as an audible alarm, to provide feedback if the subject is determined to be drowsy.

Figure 1A:
FIG. 1a is an image of a subject illuminated with a light having a wavelength of about 950 nm.
Figure 1B:
FIG. 1b is an image of a subject illuminated with a light having a wavelength of about 850 nm.

FIGS. 1a and 1b illustrate examples of first and second images of the subject 32 produced by the first and second image sensors 24, 26. FIG. 1a is an image of the subject 32 formed from light having a wavelength of about 950 nm, and FIG. 1b is an image formed from light having a wavelength of about 850 nm. FIGS. 1a and 1b are the same except that the intensity of light reflected by the retina is significantly different due to the different absorption characteristics of 950 nm light and 850 nm light.

In operation, the light source 12 produces light that is incident on the subject's eye 30. The distance between the light source 12 and the subject's eye 30 will vary depending on the particular application, but a typical distance is about three feet. That light is reflected back to the device 10 and is split by the beamsplitter 14. Part of the split light is directed towards the first filter 16, and that light is filtered by the first filter 16, focused by the first lens 20, and received by the first image sensor 24. Another part of the split light is directed towards the second filter 18, and that light is similarly filtered by the second filter 18, focused by the second lens 22, and received by the second image sensor 26. The first and second image sensors 24, 26 produce first and second signals, respectively, indicative of the images received by those image sensors 24, 26. The first and second signals are provided to the controller 28, wherein the first and second analog-to-digital converters 42, 44 convert the first and second signals from analog signals to digital signals, and provide those digital signals to the processor 40. The processor 40 subtracts one of the images, represented by one of the first and second signals, from the other of the images, represented by the other of the first and second signals, to produce a third image. Because the first and second images should be, at least for practical purposes, the same except that one of the images should include an image of the retina while the other should not include an image of the retina (or should include a more faint image of the retina), when one of the images is subtracted from the other to produce the third image, the third image should be an image of only the retina of the subject 32. The subtraction of one image from the other may be done, for example, by comparing corresponding pixels of each of the first and second images, and determining the state of the corresponding pixel in the third image. For example, if the corresponding pixels in both the first and second images is the same, either on or off, then the corresponding pixel in the third image should be off. If, however, the pixels are different, then the corresponding pixel in the third image should be on.

The present invention utilizes a property of the eye 30 to measure perclos. The present invention takes advantage of a differential reflection intensity property of the eye. In particular, the present invention utilizes the fact that the eye 30 will generally absorb light at a wavelength of about 950 nm, and the eye, more specifically the retina, will generally reflect light at other wavelengths, such as about 850 nm. The present invention illuminates the subject's eyes 30 with both frequencies of light at appropriate intensities to produce similar images, measures the reflected image at each of the wavelengths, subtracts one of the images from the other to form a third image that is primarily only of the subject's pupils. From the third image, the present invention can determine whether and to what extent the subject's eyes 30 are open (or closed). Because the third image contains much less data than a normal image of the subject, it can be processed more easily and more quickly than a conventional image of the subject. The present invention has many applications. For example, the measure of perclos is recognized by the United States Department of Transportation as the most effective means of measuring driver drowsiness. See, for example, the report to the National Highway Traffic Safety Administration, at the United States Department of Transportation, entitled *Evaluation of Techniques for Ocular Measurement as an Index of Fatigue and as the Basis for Alertness Management*, dated Apr. 1, 1998, by David F. Dinges, Ph.D, Melissa Mallis, Greg Maislin M. A., M. S., John Walker Powell, IV, M. A., which is incorporated herein by reference. In such an application, the present invention offers a significant advantage because, to be effective, determining the alertness (or drowsiness) of a driver must be done in real time.

Figure 1C:
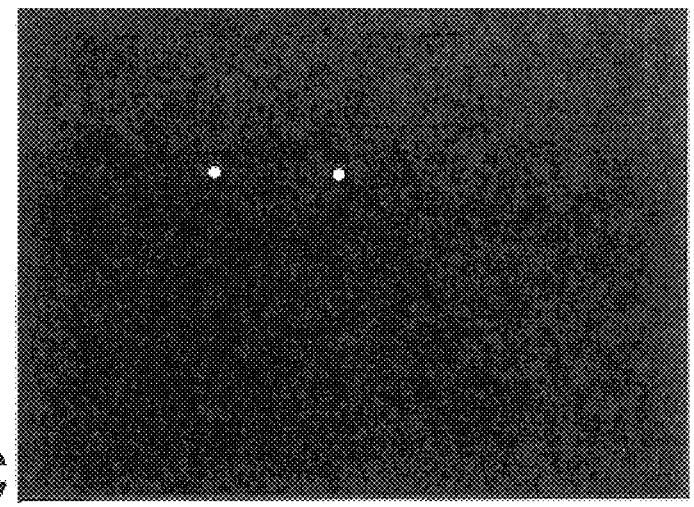
FIG. 1c is an image resulting from the image of FIG. 1a being subtracted from the image of FIG. 1b.

FIG. 1c is an example of the third image produced by the controller 28. FIG. 1c illustrates only the subject's retinas.

The third image is indicative of whether the subject's eyelids are closed, as well as the degree to which the subject's eyelids are closed.

Figure 2:
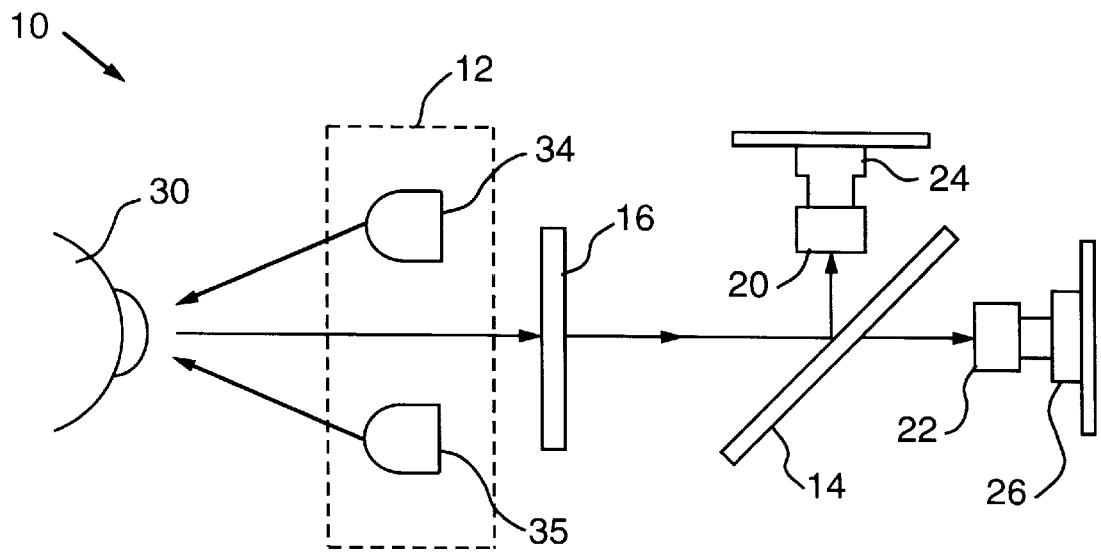
FIG. 2 is a combination block diagram and circuit schematic of a device using a single filter.

FIG. 2 is a schematic diagram of a device 10 constructed according to the present invention. The device 10 is similar to the device 10 illustrated in FIG. 1, except that the first and second filters 16, 18 are eliminated and replaced by an infrared high pass filter 16. The beamsplitter 14 may be, for example, a dichroic beamsplitter 14. The filter 16 may be located between the light source 12 and the beamsplitter 14 so that visible light does not enter the 850 nm image, and the dichroic beamsplitter 14 selectively splits the reflected light so that the first wavelength is directed to the first image sensor 24 and the second wavelength is directed to the second image sensor 26. The embodiment illustrated in FIG. 2, when equipped with a dichroic beamsplitter 14, has been found to deliver about 90% of the appropriate light to the first and second image sensors 24, 26.

Figure 3:
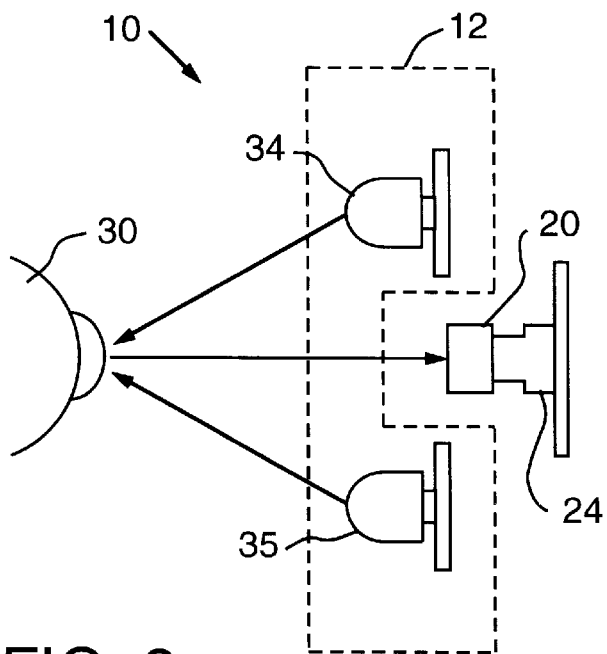
FIG. 3 is a combination block diagram and circuit schematic of a having a single image sensor.

FIG. 3 is a schematic diagram of a device 10 constructed with a single image sensor 24. That image sensor 24 differentiates between light of the first and second wavelengths with, for example, first and second filters 16, 18 (not shown) integral in the image sensor 24, as described hereinbelow with respect to FIG. 4. Alternatively, the light source 12 may strobe or modulate the first and second wavelengths of light, and the image sensor 24 may capture the alternating first and second wavelengths of reflected light. The strobing of the light source 12 and the capturing of the reflected light by the image sensor 24 may be synchronized with the synchronization signal from the controller 28. If the strobing occurs at a sufficiently high frequency, the normal movement by the subject 32 will not adversely affect the operation of the device 10. A strobing frequency of about one hundred hertz is believed to be sufficiently high for most applications.

Figure 4:
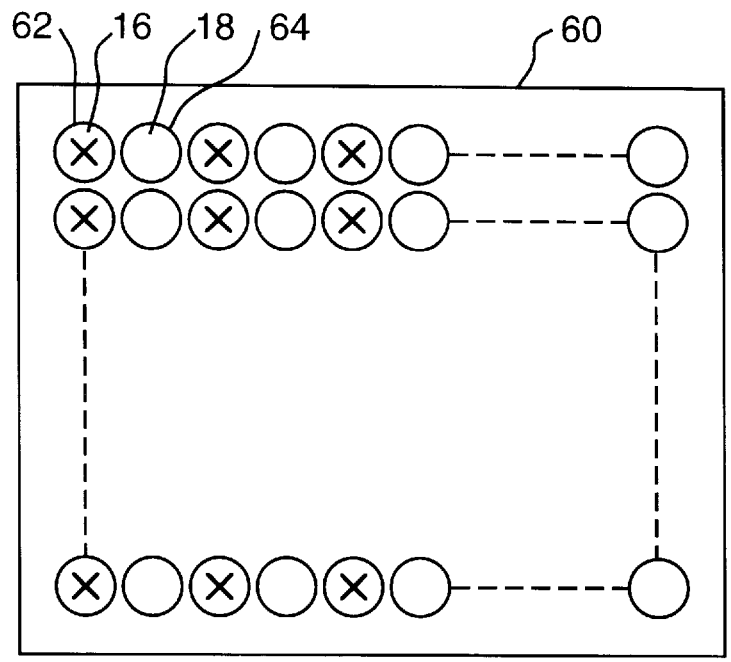
FIG. 4 is a schematic of an image plane that may be used in the image sensor illustrated in FIG. 3.

FIG. 4 is a schematic diagram illustrating an image plane 60 that may be with the image sensor 24 described with reference to FIG. 3. That image plane 60 includes a plurality of pixels 62, 64 and the first and second filters 16, 18 disposed in front of the pixels 62, 64. A plurality of the first filters 16 are in front of some of the pixels 62 and a plurality of the second filters 18 are in front of other of the pixels 64. As with the device 10 illustrated in FIGS. 1 and 2, the filters 16, 18 are selective to certain wavelengths of light so that some of the pixels 62 receive certain wavelengths of light while other of the pixels 64 receive other wavelengths of light. The filters 16, 18 may be such that the first filters 16 are in front of alternating pixels in each row, and the second filters 18 are in front of the other alternating pixels in each row. Alternatively, the first filters 16 may be in front of alternating pixels in each column, and the second filters may be in front of the other alternating pixels in each column.

Figure 5:
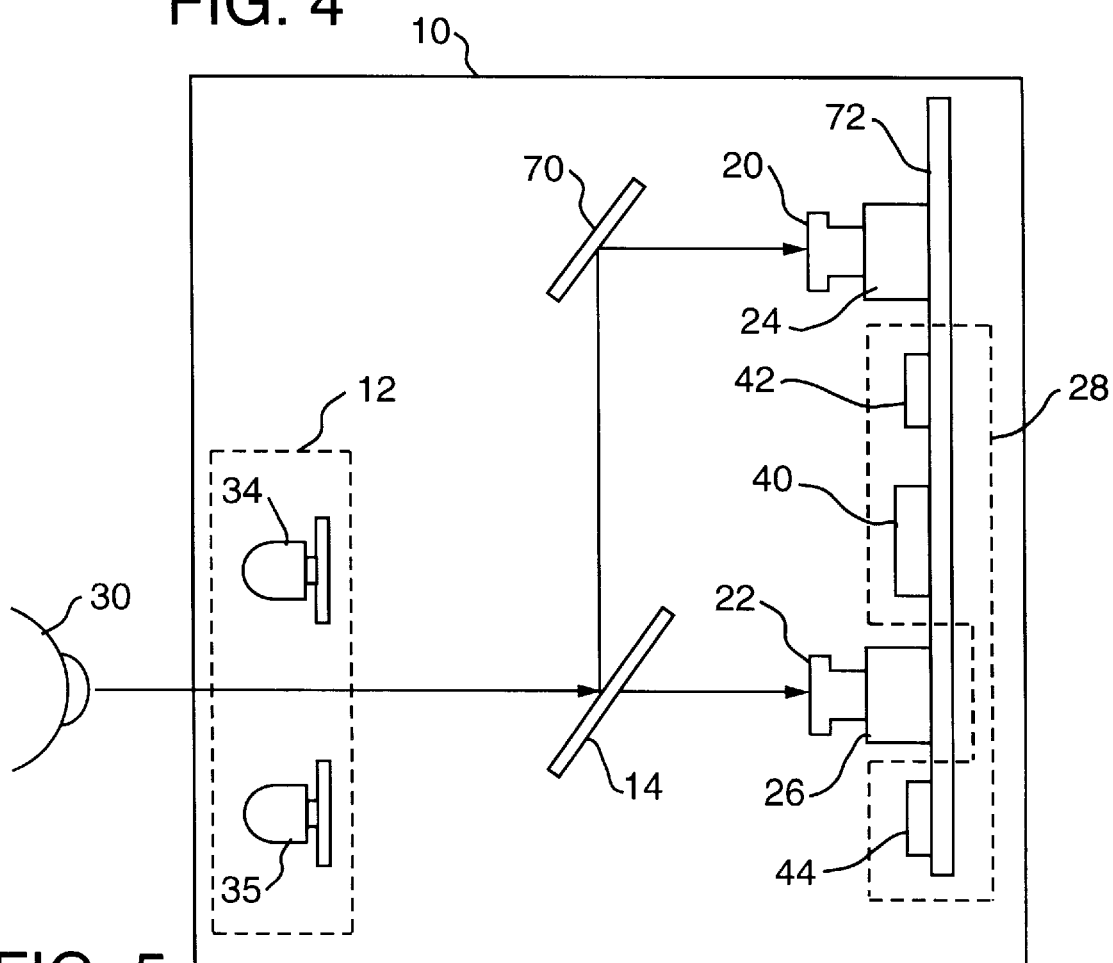
FIG. 5 is a combination block diagram and circuit schematic of a device incorporating a circuit board and mirror.

FIG. 5 is a schematic diagram illustrating a device 10 constructed according to the present invention. The beamsplitter 14 directs part of reflected light to the second image sensor 26, and another part of the reflected light is directed towards a mirror 70 and reflected towards the first image sensor 24. The first and second image sensors 24, 26 may be formed on a single substrate such as, for example, a circuit board 72. The circuit board 72 may also include the processor 40 and the first and second analog-to-digital converters 42, 44. Because the focal lengths for the first and second image sensors 24, 26 may be different, the device 10 may include first and second lens 20, 22 which are selective to the particular wavelengths intended for the first and second image sensors 24, 26, to focus the appropriate wavelengths of light on the first and second image sensors 24, 26, respectively.

The present invention also includes a method of monitoring subject's eyes 30. The method includes illuminating the subject's eyes 30 with a first wavelength of light and illuminating the subject's eyes 30 with a second wavelength of light. The first wavelength may be, for example, about 950 nm and the second wavelength may be, for example, about 850 nm. The method also includes sensing light of the first wavelength and providing a first signal indicative thereof, sensing light of the second wavelength and providing a second signal indicative thereof, and providing a third signal indicative of the first signal subtracted from the second signal. The signals may be electrical or optical, and may be analog or digital. The first and second signals may be converted from analog form to digital form, or vice versa, depending on the application. The third signal may be used to form an optical image, such as may be displayed on a display monitor 46. The method may also include providing a synchronization signal to the first and second image sensors 24, 26. If the subject 32 is, for example, determined to be drowsy, a stimuli signal may be provided. That signal may be provided to a feedback device 48, such as a audible alarm.

The method of determining the perclos may include segregating bright pixels into separate contiguous bright spots, selecting the bright spots representing each retinal reflection, calculating the luminescent centroid of each retinal reflection, measuring the vertical pixel height of each retinal reflection, selecting the largest vertical pixel measurement for each retinal reflection, and calculating a sliding window perclos value.

Those of ordinary skill in the art will recognize that many modifications and variations of the present invention may be implemented. The foregoing description and the following claims are intended to cover all such modifications and variations. Furthermore, the materials and processes disclosed are illustrative, but are not exhaustive. Other materials and processes may also be used to make devices embodying the present invention.

What is claimed is:

1. A device for monitoring a subject, comprising:

a source of light having first and second wavelengths wherein the first wavelength does not equal the second wavelength;

at least one image sensor including a plurality of pixels, the image sensor producing a first signal indicative of the plurality of pixels representing reflected light having the first wavelength and producing a second signal indicative of the plurality of pixels representing reflected light having the second wavelength; and a controller receiving the first and second signals and producing a third signal indicative of the first signal subtracted from the second signal.

2. The device of claim 1, wherein the first wavelength is 950 nm.

3. The device of claim 2, wherein the second wavelength is 850 nm.

4. The device of claim 1, wherein a ratio of light of the first wavelength reflected by the subject to light of the first wavelength absorbed by the subject is not equal to a ratio of light of the second wavelength reflected by the subject to light of the second wavelength absorbed by the subject.

5. The device of claim 1, wherein the source of light is oriented to direct light toward the subject and the at least one image sensor is oriented to receive light reflected from the subject.

6. The device of claim 5, wherein:
the source of light includes a plurality of light sources defining an opening between the plurality of light sources; and
the at least one image sensor is oriented to receive reflected light passing through the opening.

7. The device of claim 1, wherein the at least one image sensor includes a first image sensor producing the first and second signals.

8. The device of claim 1, wherein the at least one image sensor includes a first image sensor producing the first signal and a second image sensor producing the second signal.

9. The device of claim 8, wherein the first image sensor receives reflected light having the first wavelength to the exclusion of the second wavelength and the second image sensor receives light having the second wavelength to the exclusion of the first wavelength.

10. The device of claim 8, further comprising a beamsplitter oriented to split light reflected from the subject to the first and second image sensors.

11. The device of claim 10, further comprising:
a first filter between the beamsplitter and the first image sensor; and
a second filter between the beamsplitter and the second image sensor.

12. The device of claim 11, further comprising:
a first lens between the beamsplitter and the first image sensor; and
a second lens between the beamsplitter and the second image sensor.

13. The device of claim 10, further comprising a first filter, wherein the beamsplitter is oriented between the first filter and the first and second image sensors.

14. The device of claim 13, further comprising:
a first lens between the beamsplitter and the first image sensor; and
a second lens between the beamsplitter and the second image sensor.

15. The device of claim 10, further comprising a mirror oriented to reflect light from the beamsplitter to the first image sensor.

16. The device of claim 15, further comprising:
a first lens between the mirror and the first image sensor; and
a second lens between the beamsplitter and the second image sensor.

17. The device of claim 8, wherein the first and second image sensors simultaneously capture an image of the subject.

18. The device of claim 17, wherein the controller provides a synchronization signal to each of the first and second image sensors.

19. The device of claim 1, wherein the controller includes:
a converter having an input terminal coupled to the at least one image sensor; and
a processor coupled to the converter.

20. The device of claim 1, further comprising a video monitor in communication with the controller.

21. The device of claim 1, further comprising a feedback device in communication with the controller.

22. The device of claim 1, wherein the image sensor is selected from the group consisting of a CCD image sensor and a CMOS-type image sensor.

23. A device for monitoring a subject's eyes, comprising:
a source of light oriented to direct light toward the subject's eyes, the light having first and second wavelengths, wherein the first wavelength does not equal the second wavelength;
a first image sensor;
a second image sensor;
a beamsplitter oriented to split light reflected from the subject's eyes to the first and second image sensor;
a first filter between the beamsplitter and the first image sensor;
a second filter between the beamsplitter and the second image sensor; and
a controller in communication with the first and second image sensors.

24. The device of claim 23, wherein the first image sensor produces a first signal indicative of reflected light having the first wavelength, the second image sensor produces a second signal indicative of reflected light having the second wavelength, and the controller produces a third signal indicative of the first signal subtracted from the second signal.

25. A device for monitoring a subject's eyes, comprising:
a source of light oriented to transmit light toward the subject's eyes, the light having first and second wavelengths, wherein the first wavelength does not equal the second wavelength;
a first image sensor;
a second image sensor;
a beamsplitter oriented to split light reflected from the subject's eyes to the first and second image sensors;
a first filter oriented to filter light reflected by the subject's eyes before being split by the beamsplitter; and
a controller in communication with the first and second image sensors.

26. The device of claim 25, wherein the first filter is an infrared high pass filter and wherein the beamsplitter is a dichroic beamsplitter.

27. The device of claim 25, wherein the first image sensor produces a first signal indicative of reflected light having the first wavelength, the second image sensor produces a second signal indicative of reflected light having the second wavelength, and the controller produces a third signal indicative of the first signal subtracted from the second signal.

28. A device for monitoring a subject's eyes, comprising:
a source of light oriented to transmit light toward the subject's eyes, the light having first and second wavelengths, wherein the first wavelength does not equal the second wavelength;
a first image sensor;
a second image sensor;
a beamsplitter oriented to split light reflected from the subject's eyes to the first and second image sensors;
a mirror oriented to reflect light from the beamsplitter to the first image sensor; and
a controller in communication with the first and second image sensors.

29. The device of claim 28, wherein the first image sensor produces a first signal indicative of reflected light having the first wavelength, the second image sensor produces a second signal indicative of reflected light having the second wavelength, and the controller produces a third signal indicative of the first signal subtracted from the second signal.

30. A device, comprising:
a source of light oriented to transmit light toward a subject, the light having first and second wavelengths wherein the first wavelength does not equal the second wavelength;

means for producing a first signal indicative of a plurality of pixels representing light reflected by the subject having the first wavelength;

means for producing a second signal indicative of a plurality of pixels representing light reflected by the subject having the second wavelength; and means for producing a third signal indicative of the first signal subtracted from the second wavelength.

31. The device of claim 30, further comprising means for separating reflected having the first wavelength from reflected light having the second wavelength.

32. The device of claim 30, wherein the means for producing a first signal include means for capturing a first image of the subject and the means for producing a second signal includes means for capturing a second image of the subject.

33. The device of claim 32, further comprising means for simultaneously capturing the first and second images.

34. A method, comprising:

directing light having a first wavelength toward a subject;

directing light having a second wavelength toward the subject, wherein the first wavelength does not equal the second wavelength;

capturing a first image of light reflected by the subject and having the first wavelength, wherein the first image is represented as a plurality of pixels;

capturing a second image of light reflected by the subject and having the second wavelength, wherein the second image is represented as a plurality of pixels; and subtracting a signal indicative of the first image from a signal indicative of the second image.

35. The method of claim 34, wherein directing light having the first wavelength and directing light having the second wavelength includes simultaneously directing light having the first and second wavelengths.

36. The method of claim 35, wherein capturing the first image and capturing the second image includes simultaneously capturing the first and second images.

37. The method of claim 34, wherein directing light having the first wavelength and directing light having the second wavelength includes consecutively directing light having the first wavelength and light having the second wavelength.

38. The method of claim 37, wherein capturing the first image and capturing the second image include consecutively capturing the first and second images.

39. The method of claim 34, further comprising separating light reflected from the subject having the first wavelength from light reflected from the subject having the second wavelength.

40. A method of for monitoring a subject's eyes, comprising:

illuminating the subject's eyes with light having a first wavelength;

illuminating the subject's eyes with light having a second wavelength, wherein the first wavelength does not equal the second wavelength;

sensing light of the first wavelength reflected by the subject's eyes;

sensing light of the second wavelength reflected by the subject's eyes;

providing a first signal indicative of the sensed light having the first wavelength;

providing a second signal indicative of the sensed light having the second wavelength; and providing a third signal indicative of the first signal subtracted from the second signal.

41. The method of claim 40, wherein illuminating with light having the first wavelength and illuminating with light having the second wavelength includes simultaneously illuminating the subject's eyes with light having the first and second wavelengths.

42. The method of claim 41, wherein sensing light of the first wavelength and sensing light of the second wavelength includes simultaneously sensing light having the first and second wavelengths.

43. The method of claim 40, wherein illuminating the subject's eyes with light having the first wavelength includes illuminating the subject's eyes with light having a wavelength of 850 nm, and illuminating the subject's eyes with light having the second wavelength includes illuminating the subject's eyes with light having a wavelength of 950 nm.

44. The method of claim 40, wherein illuminating with light having the first wavelength and illuminating with light having the second wavelength includes consecutively illuminating the subject's eyes with light having the first wavelength and illuminating the subject's eyes with light having the second wavelength.

45. The method of claim 44, wherein sensing light of the first wavelength and sensing light of the second wavelength includes consecutively sensing light having the first wavelength and sensing light having the second wavelength.

46. A device for monitoring a subject, comprising:

a source of light having first and second wavelengths wherein the first wavelength does not equal the second wavelength;

at least one image sensor producing a first signal indicative of a reflected image of the subject in the form of light having the first wavelength and producing a second signal indicative of a reflected image of the subject in the form of light having the second wavelength; and a controller receiving the first and second signals and producing a third signal indicative of the first signal subtracted from the second signal.

47. The device of claim 46, wherein the image sensor is selected from the group consisting of a CCD image sensor and a CMOS-type image sensor.

48. The device of claim 46, wherein the first wavelength is 950 nm.

49. The device of claim 48, wherein the second wavelength is 850 nm.

50. The device of claim 46, wherein a ratio of light of the first wavelength reflected by the subject to light of the first wavelength absorbed by the subject is not equal to a ratio of light of the second wavelength reflected by the subject to light of the second wavelength absorbed by the subject.

51. The device of claim 46, wherein the source of light is oriented to direct light toward the subject and the at least one image sensor is oriented to receive light reflected from the subject.

52. The device of claim 51, wherein:

the source of light includes a plurality of light sources defining an opening between the plurality of light sources; and the at least one image sensor is oriented to receive reflected light passing through the opening.

53. The device of claim 46, wherein the controller includes:
- a converter having an input terminal coupled to the at least one image sensor; and
- a processor coupled to the converter.

54. A device, comprising:
- a source of light oriented to transmit light toward a subject, the light having first and second wavelengths wherein the first wavelength does not equal the second wavelength;
- means for receiving a first image of the subject from light reflected by the subject having the first wavelength;
- means for receiving a second image of the subject from light reflected by the subject having the second wavelength;
- means for producing a first signal indicative of the first image;
- means for producing a second signal indicative of second image; and
- means for producing a third signal indicative of the first signal subtracted from the second signal.

55. A method, comprising:
- directing light having a first wavelength toward a subject;
- directing light having a second wavelength toward the subject, wherein the first wavelength does not equal the second wavelength;
- capturing a first image in the form of light reflected by the subject and having the first wavelength;
- capturing a second image in the form of light reflected by the subject and having the second wavelength; and
- producing a signal indicative of the first image subtracted from the second image.

56. The method of claim 55, wherein directing light having the first wavelength and directing light having the second wavelength includes simultaneously directing light having the first and second wavelengths.

57. The method of claim 56, wherein capturing the first image and capturing the second image includes simultaneously capturing the first and second images.

58. The method of claim 55, wherein directing light having the first wavelength and directing light having the second wavelength includes consecutively directing light having the first wavelength and light having the second wavelength.

59. The method of claim 58, wherein capturing the first image and capturing the second image include consecutively capturing the first and second images.

60. The method of claim 55, further comprising separating light reflected from the subject having the first wavelength from light reflected from the subject having the second wavelength.

61. A method, comprising:
- directing light having a first wavelength toward a subject;
- directing light having a second wavelength toward the subject, wherein the first wavelength does not equal the second wavelength;
- capturing a first image of light reflected by the subject and having the first wavelength, wherein the first image is represented as a plurality of pixels;
- capturing a second image of light reflected by the subject and having the second wavelength, wherein the second image is represented as a plurality of pixels; and
- producing a signal indicative of the first image subtracted from the second image.

* * * * *